United States Patent [19]

Peery et al.

[11] Patent Number: 6,074,847
[45] Date of Patent: Jun. 13, 2000

[54] STREPTOCOCCUS PNEUMONIAE GENE SEQUENCE HI1146

[75] Inventors: Robert Brown Peery, Brownsburg; Paul Luther Skatrud; Patti Jean Treadway, both of Greenwood; Michele Louise Young Bellido, Indianapolis, all of Ind.

[73] Assignee: Eli Lilly and Company, Indianapolis, Ind.

[21] Appl. No.: 08/986,769

[22] Filed: Dec. 8, 1997

Related U.S. Application Data

[60] Provisional application No. 60/036,281, Dec. 13, 1996.
[51] Int. Cl.[7] ........................................................ C12P 21/06
[52] U.S. Cl. .................... 435/69.3; 435/320.1; 435/69.1; 435/71.1; 435/71.2; 435/440; 435/471; 435/252.3; 435/254.11; 435/257.2; 435/822; 536/23.1; 536/23.7; 536/24.32
[58] Field of Search ................................ 435/320.1, 69.1, 435/69.3, 71.1, 71.2, 440, 471, 252.3, 254.11, 257.2, 822; 536/23.1, 23.7, 24.32

[56] References Cited

PUBLICATIONS

Lindler et al. 1987. J. Bacteriol. 169(7): 3199–3208.
S. Natagene. 1991. Product Catalogue p. 292.
Boehringer Mannheim Biochemicals 1991 Catalog p. 557.
Promega 1993/4 Catalog pp. 90–91.
New England Biolabs Catalog 1986/7, pp. 60–62.
Fleischmann, et al. "Whole–Genome Random Sequencing and Assembly of *Haemophilus influenzae* Rd." *Science* 269:496–512 (Jul. 28, 1995).

*Primary Examiner*—Christopher L. Chin
*Assistant Examiner*—Jennifer Graser
*Attorney, Agent, or Firm*—Raymond S. Parker III; Thomas D. Webster

[57] ABSTRACT

The invention provides isolated nucleic acid compounds encoding HI1146 of *Streptococcus pneumoniae*. Also provided are vectors and transformed host cells for expressing the encoded protein, and a method for identifying compounds that bind and/or inhibit said protein.

12 Claims, No Drawings

6,074,847

STREPTOCOCCUS PNEUMONIAE GENE SEQUENCE HI1146

This application claims the benefit of U.S. Provisional Application No. 60/036,281, filed Dec. 13, 1996.

BACKGROUND OF THE INVENTION

This invention provides isolated DNA sequences, proteins encoded thereby, and methods of using said DNA and protein in a variety of applications.

Widespread antibiotic resistance in common pathogenic bacterial species has justifiably alarmed the medical and research communities. Frequently, resistant organisms are co-resistant to several antibacterial agents. Penicillin resistance in *Streptococcus pneumoniae* has been particularly problematic. This organism causes upper respiratory tract infections. Modification of a penicillin-binding protein (PBP) underlies resistance to penicillin in the majority of cases. Combating resistance to antibiotic agents will require research into the molecular biology of pathogenic organisms. The goal of such research will be to identify new antibacterial agents.

While researchers continue to develop antibiotics effective against a number of microorganisms, *Streptococcus pneumoniae* has been more refractory. In part, this is because *Streptococcus pneumoniae* is highly recombinogenic and readily takes up exogenous DNA from its surroundings. Thus, there is a need for new antibacterial compounds and new targets for antibacterial therapy in *Streptococcus pneumoniae*.

BRIEF SUMMARY OF THE INVENTION

The present invention relates to an isolated gene and encoded protein from *S. pneumoniae*. The invention enables: (1) preparation of probes and primers for use in hybridizations and PCR amplifications, (2) production of proteins and RNAs encoded by said gene and related nucleic acids, and (3) methods to identify compounds that bind and/or inhibit said protein(s).

In one embodiment the present invention relates to an isolated nucleic acid molecule encoding HI1146 protein.

In another embodiment, the invention relates to a nucleic acid molecule comprising the nucleotide sequence identified as SEQ ID NO:1, SEQ ID NO:3, or SEQ ID NO:4.

In another embodiment, the present invention relates to a nucleic acid that encodes SEQ ID NO:2.

In another embodiment the present invention relates to an isolated protein molecule, wherein said protein molecule comprises the sequence identified as SEQ ID NO:2.

In yet another embodiment, the present invention relates to a recombinant DNA vector that incorporates the HI1146 gene in operable linkage to gene expression sequences enabling the gene to be transcribed and translated in a host cell.

In still another embodiment the present invention relates to host cells that have been transformed or transfected with the cloned HI1146 gene such that said gene is expressed in the host cell.

This invention also provides a method of determining whether a nucleic acid sequence of the present invention, or fragment thereof, is present in a sample, comprising contacting the sample, under suitable hybridization conditions, with a nucleic acid probe of the present invention.

In a still further embodiment, the present invention relates to a method for identifying compounds that bind and/or inhibit the HI1146 protein.

DETAILED DESCRIPTION OF THE INVENTION

"ORF" (i.e. "open reading frame") designates a region of genomic DNA beginning with a Met or other initiation codon and terminating with a translation stop codon, that potentially encodes a protein product. "Partial ORF" means a portion of an ORF as disclosed herein such that the initiation codon, the stop codon, or both are not disclosed.

"Consensus sequence" refers to an amino acid or nucleotide sequence that may suggest the biological function of a protein, DNA, or RNA molecule. Consensus sequences are identified by comparing proteins, RNAs, and gene homologues from different species.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

"Essential genes" or "essential ORFs" or "essential proteins" refer to genomic information or the protein(s) or RNAs encoded thereby, that when disrupted by knockout mutation, or by other mutation, result in a loss of viability of cells harboring said mutation.

"Non-essential genes" or "non-essential ORFs" or "non-essential proteins" refer to genomic information or the protein(s) or RNAs encoded therefrom which when disrupted by knockout mutation, or other mutation, do not result in a loss of viability of cells harboring said mutation.

"Minimal gene set" refers to a genus comprising about 256 genes conserved among different bacteria such as *M. genitalium* and *H. influenzae*. The minimal gene set may be necessary and sufficient to sustain life. See e.g. A. Mushegian and E. Koonin, "A minimal gene set for cellular life derived by comparison of complete bacterial genomes" Proc. Nat. Acad. Sci. 93, 10268–273 (1996).

"Knockout mutant" or "knockout mutation" as used herein refers to an in vitro engineered disruption of a region of native chromosomal DNA, typically within a protein coding region, such that a foreign piece of DNA is inserted within the native sequence. A knockout mutation occurring in a protein coding region prevents expression of the wild-type protein. This usually leads to loss of the function provided by the protein. A "knockout cassette" refers to a fragment of native chromosomal DNA having cloned therein a foreign piece of DNA that may provide a selectable marker.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refer to the capacity of purine and pyrimidine nucleotides to associate through hydrogen bonding to form double stranded nucleic acid molecules. The following base pairs are related by complementarity: guanine and cytosine; adenine and thymine; and adenine and uracil. As used herein, "complementary" applies to all base pairs comprising two single-stranded nucleic acid molecules. "Partially complementary" means one of two single-stranded nucleic acid molecules is shorter than the other, such that one of the molecules remains partially single-stranded.

"Oligonucleotide" refers to a short nucleotide chain comprising from about 2 to about 25 nucleotides.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which can be used to hybridize with another nucleic acid compound.

The term "hybridization" or "hybridize" as used herein refers to the process by which a single-stranded nucleic acid molecule joins with a complementary strand through nucleotide base pairing.

"Substantially purified" as used herein means a specific isolated nucleic acid or protein, or fragment thereof, in which substantially all contaminants (i.e. substances that differ from said specific molecule) have been separated from said nucleic acid or protein. For example, a protein may, but not necessarily, be "substantially purified" by the IMAC method as described herein.

"Selective hybridization" refers to hybridization under conditions of high stringency. The degree of hybridization between nucleic acid molecules depends upon, for example, the degree of complementarity, the stringency of hybridization, and the length of hybridizing strands.

The term "stringency" relates to nucleic acid hybridization conditions. High stringency conditions disfavor non-homologous base pairing. Low stringency conditions have the opposite effect. Stringency may be altered, for example, by changes in temperature and salt concentration. Typical high stringency conditions comprise hybridizing at 50° C. to 65° C. in 5×SSPE and 50% formamide, and washing at 50° C. to 65° C. in 0.5×SSPE; typical low stringency conditions comprise hybridizing at 35° C. to 37° C. in 5×SSPE and 40% to 45% formamide and washing at 42° C. in 1–×2×SSPE.

"SSPE" denotes a hybridization and wash solution comprising sodium chloride, sodium phosphate, and EDTA, at pH 7.4. A 20× solution of SSPE is made by dissolving 174 g of NaCl, 27.6 g of $NaH_2PO_4.H_2O$, and 7.4 g of EDTA in 800 ml of $H_2O$. The pH is adjusted with NaOH and the volume brought to 1 liter.

"SSC" denotes a hybridization and wash solution comprising sodium chloride and sodium citrate at pH 7. A 20× solution of SSC is made by dissolving 175 g of NaCl and 88 g of sodium citrate in 800 ml of $H_2O$. The volume is brought to 1 liter after adjusting the pH with 10N NaOH.

DETAILED DESCRIPTION OF THE INVENTION

The HI1146 gene disclosed herein (SEQ ID NO:1) and related nucleic acids (e.g. SEQ ID NO:3 and SEQ ID NO:4) encode an essential integral membrane protein of 70.7 kDa that has an AAA-type ATPase domain at its C-terminus. HI1146 is involved in degradation of the heat-shock transcription factor sigma 32.

The proteins categorized as "minimal gene set" counterparts are homologous to a set of highly conserved proteins found in other bacteria. The minimal gene set proteins are thought to be essential for viability and are useful targets for the development of new antibacterial compounds.

In one embodiment, the proteins of this invention are purified, and used in a screen to identify compounds that bind and/or inhibit the activity of said proteins. A variety of suitable screens are contemplated for this purpose. For example, the protein(s) can be labeled by known techniques, such as radiolabeling or fluorescent tagging, or by labeling with biotin/avidin. Thereafter, binding of a test compound to a labeled protein can be determined by any suitable means, well known to the skilled artisan.

Skilled artisans will recognize that the DNA molecules of this invention, or fragments thereof, can be generated by general cloning methods. PCR amplification using oligonucleotide primers targeted to any suitable region of SEQ ID NO:1 is preferred. Methods for PCR amplification are widely known in the art. See e.g. *PCR Protocols: A Guide to Method and Application*, Ed. M. Innis et al., Academic Press (1990) or U.S. Pat. No. 4,889,818, which hereby is incorporated by reference. A PCR comprises DNA, suitable enzymes, primers, and buffers, and is conveniently carried out in a DNA Thermal Cycler (Perkin Elmer Cetus, Norwalk, Conn.). A positive PCR result is determined by, for example, detecting an appropriately-sized DNA fragment following agarose gel electrophoresis.

The DNAs of the present invention may also be produced using synthetic methods well known in the art. (See, e.g., E. L. Brown, R. Belagaje, M. J. Ryan, and H. G. Khorana, *Methods in Enzymology*, 68:109–151 (1979)). An apparatus such as the Applied Biosystems Model 380A or 380B DNA synthesizers (Applied Biosystems, Inc., 850 Lincoln Center Drive, Foster City, Calif. 94404) may be used to synthesize DNA. Synthetic methods rely upon phosphotriester chemistry [See, e.g., M. J. Gait, ed., *Oligonucleotide Synthesis, A Practical Approach*, (1984)], or phosphoramidite chemistry.

Protein Production Methods

The present invention relates further to substantially purified proteins encoded by the gene disclosed herein.

Skilled artisans will recognize that proteins can be synthesized by different methods, for example, chemical methods or recombinant methods, as described in U.S. Pat. No. 4,617,149, which hereby is incorporated by reference.

The principles of solid phase chemical synthesis of polypeptides are well known in the art and may be found in general texts relating to this area. See, e.g., H. Dugas and C. Penney, *Bioorganic Chemistry* (1981) Springer-Verlag, New York, 54–92. Peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

The proteins of the present invention can also be made by recombinant DNA methods. Recombinant methods are preferred if a high yield is desired. Recombinant methods involve expressing the cloned gene in a suitable host cell. The gene is introduced into the host cell by any suitable means, well known to those skilled in the art. While chromosomal integration of the cloned gene is within the scope of the present invention, it is preferred that the cloned gene be maintained extra-chromosomally, as part of a vector in which the gene is in operable-linkage to a promoter.

Recombinant methods can also be used to overproduce a membrane-bound or membrane-associated protein. In some cases, membranes prepared from recombinant cells expressing such proteins provide an enriched source of the protein.
Expressing Recombinant Proteins in Procaryotic and Eucaryotic Host Cells Procaryotes are generally used for cloning DNA sequences and for constructing vectors. For example, the *Escherichia coli* K12 strain 294 (ATCC No. 31446) is particularly useful for expression of foreign proteins. Other strains of *E. coli*, bacilli such as *Bacillus subtilis*, enterobacteriaceae such as *Salmonella typhimurium* or *Serratia marcescans*, various Pseudomonas species may also be employed as host cells in cloning and expressing the recombinant proteins of this invention. Also contemplated are various strains of Streptococcus and Streptocmyces.

For effective recombinant protein production, a gene must be linked to a promoter sequence. Suitable bacterial promoters include b -lactamase [e.g. vector pGX2907, ATCC 39344, contains a replicon and b -lactamase gene], lactose systems [Chang et al., *Nature* (London), 275:615 (1978); Goeddel et al., *Nature* (London), 281:544 (1979)], alkaline phosphatase, and the tryptophan (trp) promoter system [vector pATH1 (ATCC 37695)] designed for the iexpression of a trpE fusion protein. Hybrid promoters such as the tac promoter (isolatable from plasmid pDR540, ATCC-37282) are also suitable. Promoters for use in bacterial systems also will contain a Shine-Dalgarno sequence, operably linked to the DNA encoding the desired polypeptides. These examples are illustrative rather than limiting.

A variety of mammalian cells and yeasts are also suitable hosts. The yeast *Saccharomyces cerevisiae* is commonly used. Other yeasts, such as *Kluyveromyces lactis*, are also suitable. For expression of recombinant genes in Saccharomyces, the plasmid YRp7 (ATCC-40053), for example, may be used. See, e.g., L. Stinchcomb, et al., *Nature*, 282:39 (1979); J. Kingsman et al., *Gene*, 7:141 (1979); S. Tschemper et al., *Gene*, 10:157 (1980). Plasmid YRp7 contains the TRP1 gene, a selectable marker for a trp1 mutant.

Purification of Recombinantly-Produced Protein

An expression vector carrying a nucleic acid or gene of the present invention is transformed or transfected into a suitable host cell using standard methods. Cells that contain the vector are propagated under conditions suitable for expression of a recombinant protein. For example, if the gene is under the control of an inducible promoter, then suitable growth conditions would incorporate the appropriate inducer. The recombinantly-produced protein may be purified from cellular extracts of transformed cells by any suitable means.

In a preferred process for protein purification a gene is modified at the 5' end, or at some other position, such that the encoded protein incorporates several histidine residues (viz. "histidine tag"). This "histidine tag" enables "immobilized metal ion affinity chromatography" (IMAC), a single-step protein purification method described in U.S. Pat. No. 4,569,794, which hereby is incorporated by reference. The IMAC method enables isolation of substantially pure protein starting from a crude cellular extract.

As skilled artisans will recognize, owing to the degeneracy of the code, the proteins of the invention can be encoded by a large genus of different nucleic acid sequences. This invention further comprises said genus.

The ribonucleic acid compounds of the invention may be prepared using the polynucleotide synthetic methods discussed supra, or they may be prepared enzymatically using RNA polymerase to transcribe a DNA template.

The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5' end of a template. See, J. Sambrook, et al., supra, at 18.82–18.84.

This invention also provides nucleic acids that are complementary to the sequences disclosed herein.

The present invention also provides probes and primers, useful for a variety of molecular biology techniques including, for example, hybridization screens of genomic or subgenomic libraries, or detection and quantification of mRNA species as a means to analyze gene expression. A nucleic acid compound is provided comprising any of the sequences disclosed herein, or a complementary sequence thereof, or a fragment thereof, which is at least 15 base pairs in length, and which will hybridize selectively to *Streptococcus pneumoniae* DNA or mRNA. Preferably, the 15 or more base pair compound is DNA. A probe or primer length of at least 15 base pairs is dictated by theoretical and practical considerations. See e.g. B. Wallace and G. Miyada, "Oligonucleotide Probes for the Screening of Recombinant DNA Libraries," In *Methods in Enzymology*, Vol. 152, 432–442, Academic Press (1987).

The probes and primers of this invention can be prepared by methods well known to those skilled in the art (See e.g. Sambrook et al. supra). In a preferred embodiment the probes and primers are synthesized by the polymerase chain reaction (PCR).

The present invention also relates to recombinant DNA cloning vectors and expression vectors comprising the nucleic acids of the present invention. Preferred nucleic acid vectors are those that comprise DNA. The skilled artisan understands that choosing the most appropriate cloning vector or expression vector depends on the availability of restriction sites, the type of host cell into which the vector is to be transfected or transformed, the purpose of transfection or transformation (e.g., stable transformation as an extrachromosomal element, or integration into a host chromosome), the presence or absence of readily assayable or selectable markers (e.g., antibiotic resistance and metabolic markers of one type and another), and the number of gene copies desired in the host cell.

Suitable vectors comprise RNA viruses, DNA viruses, lytic bacteriophages, lysogenic bacteriophages, stable bacteriophages, plasmids, viroids, and the like. The most preferred vectors are plasmids.

Host cells harboring the nucleic acids disclosed herein are also provided by the present invention. A preferred host is *E. coli* transfected or transformed with a vector comprising a nucleic acid of the present invention.

The invention also provides a host cell capable of expressing a gene described herein, said method comprising transforming or otherwise introducing into a host cell a recombinant DNA vector comprising an isolated DNA sequence that encodes said gene. The preferred host cell is any strain of E. coli that can accommodate high level expression of an exogenously introduced gene. Transformed host cells are cultured under conditions well known to skilled artisans, such that said gene is expressed, thereby producing the encoded protein in the recombinant host cell.

To discover compounds having antibacterial activity, one can look for agents that inhibit cell growth and/or viability by, for example, inhibiting enzymes required for cell wall biosynthesis, and/or by identifying agents that interact with membrane proteins. A method for identifying such compounds comprises contacting a suitable protein or membrane preparation with a test compound and monitoring by any suitable means an interaction and/or inhibition of a protein of this invention.

For example, the instant invention provides a screen for compounds that interact with the proteins of the invention, said screen comprising:

a) preparing a protein, or membranes enriched in a protein;

b) exposing the protein or membranes to a test compound; and c) detecting an interaction of a protein with said compound by any suitable means.

The screening method of this invention may be adapted to automated procedures such as a PANDEX® (Baxter-Dade Diagnostics) system, allowing for efficient high-volume screening of compounds.

In a typical screen, a protein is prepared as idescribed herein, preferably using recombinant DNA technology. A test compound is introduced into a reaction vessel containing said protein. The reaction/interaction of said protein and said compound is monitored by any suitable means. In a preferred method, a radioactively-labeled or chemically-labeled compound or protein is used. A specific association between the test compound and protein is monitored by any suitable means.

In such a screening protocol HI1146 is prepared as described herein, preferably using recombinant DNA technology. A test compound is introduced into a reaction vessel containing the HI1146 protein or fragment thereof. Binding of HI1146 by a test compound is determined by any suitable means. For example, in one method radioactively-labeled or chemically-labeled test compound may be used. Binding of the protein by the compound is assessed, for example, by quantifying bound label versus unbound label using any suitable method. Binding of a test compound may also be carried out by a method disclosed in U.S. Pat. No. 5,585, 277, which hereby is incorporated by reference. In this method, binding of a test compound to a protein is assessed by monitoring the ratio of folded protein to unfolded protein, for example by monitoring sensitivity of said protein to a protease, or amenability to binding of said protein by a specific antibody against the folded state of the protein.

The foregoing screening methods are useful for identifying a ligand of a HI1146 protein, perhaps as a lead to a pharmaceutical compound for modulating the state of differentiation of an appropriate tissue. A ligand that binds HI1146, or related fragment thereof, is identified, for example, by combining a test ligand with HI1146 under conditions that cause the protein to exist in a ratio of folded to unfolded states. If the test ligand binds the folded state of the protein, the relative amount of folded protein will be higher than in the case of a test ligand that does not bind the protein. The ratio of protein in the folded versus unfolded state is easily determinable by, for example, susceptibility to digestion by a protease, or binding to a specific antibody, or binding to chaperonin protein, or binding to any suitable surface.

The following examples more fully describe the present invention. Those skilled in the art will recognize that the particular reagents, equipment, and procedures described are merely illustrative and are not intended to limit the present invention in any manner.

EXAMPLE 1

Production of a Vector for Expressing S. pneumoniae HI1146 in a Host Cell

An expression vector suitable for expressing S. pneumoniae HI1146 in a variety of procaryotic host cells, such as E. coli, is easily made. The vector contains an origin of replication (Ori), an ampicillin resistance gene (Amp) useful for selecting cells which have incorporated the vector following a tranformation procedure, and further comprises the T7 promoter and T7 terminator sequences in operable linkage to the HI1146 coding region. Plasmid pET11A (obtained from Novogen, Madison, Wis.) is a suitable parent plasmid. pET11A is linearized by restriction with endonucleases NdeI and BamHI. Linearized pET11A is ligated to a DNA fragment bearing NdeI and BamHI sticky ends and comprising the coding region of the S. pneumoniae HI1146 (SEQ ID NO:1). The coding region for HI1146 is easily produced by PCR technology using suitably designed primers to the ends of the coding region specified in SEQ ID NO:1.

The HI1146 encoding nucleic acid used in this construct is slightly modified at the 5' end (amino terminus of encoded protein) in order to simplify purification of the encoded protein product. For this purpose, an oligonucleotide encoding 8 histidine residues is inserted after the ATG start codon. Placement of the histidine residues at the amino terminus of the encoded protein serves to enable the IMAC one-step protein purification procedure.

EXAMPLE 2

Recombinant Expression and Purification of a Protein Encoded by S. pneumoniae HI1146

An expression vector that carries HI1146 from the S. pneumoniae genome as disclosed herein and which HI1146 is operably-linked to an expression promoter is transformed into E. coli BL21 (DE3)(hsdS gal lcIts857 ind1Sam7nin5lacUV5-T7gene 1) using standard methods (see Example 4). Transformants, selected for resistance to ampicillin, are chosen at random and tested for the presence of the vector by agarose gel electrophoresis using quick plasmid preparations. Colonies which contain the vector are grown in L broth and the protein product encoded by the vector-borne ORF is purified by immobilized metal ion affinity chromatography (IMAC), essentially as described in U.S. Pat. No. 4,569,794.

Briefly, the IMAC column is prepared as follows. A metal-free chelating resin (e.g. Sepharose 6B IDA, Pharmacia) is washed in distilled water to remove preservative substances and infused with a suitable metal ion [e.g. Ni(II), Co(II), or Cu(II)] by adding a 50 mM metal chloride or metal sulfate aqueous solution until about 75% of the interstitial spaces of the resin are saturated with colored metal ion. The column is then ready to receive a crude cellular extract containing the recombinant protein product.

After removing unbound proteins and other materials by washing the column with any suitable buffer, pH 7.5, the bound protein is eluted in any suitable buffer at pH 4.3, or preferably with an imidizole-containing buffer at pH 7.5.

We claim:

1. An isolated nucleic acid compound encoding the protein of SEQ ID NO:2.

2. An isolated nucleic acid compound, wherein the sequence of said compound is selected from the group consisting of:
   (a) SEQ ID NO:1;
   (b) SEQ ID NO:3; and
   (c) a nucleic acid compound fully complementary to (a) or (b).

3. An isolated nucleic acid compound, wherein the sequence of said compound is SEQ ID NO:4.

4. An isolated nucleic acid compound of claim 2 wherein the sequence of said compound is SEQ ID NO:1 or a sequence fully complementary to SEQ ID NO: 1.

5. An isolated nucleic acid compound of claim 2 wherein the sequence of said compound is SEQ ID NO:3 or a sequence fully complementary to SEQ ID NO:3.

6. An isolated nucleic acid compound that hybridizes to SEQ ID NO:1 or SEQ ID NO:3 under high stringency conditions.

7. A vector comprising an isolated nucleic acid compound of claim 2.

8. A vector, as in claim 7, wherein said isolated nucleic acid compound is SEQ ID NO:1, operably-linked to a promoter sequence.

9. A host cell containing a vector of claim 7.

10. A host cell containing a vector of claim 8.

11. A method for constructing a recombinant host cell that expresses SEQ ID NO:2, said method comprising introducing into said host cell by any suitable means a vector of claim 8.

12. A method for expressing SEQ ID NO:2 in the recombinant host cell of claim 11, said method comprising culturing said recombinant host cell under conditions suitable for gene expression.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 891 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 1..891

(xi) SEQUENCE DESCRIPTION: SEQ ID NO:1:

```
ATG ACA AAG AAA CAA CTT CAC TTG GTG ATT GTG ACA GGG ATG GGT GGC      48
Met Thr Lys Lys Gln Leu His Leu Val Ile Val Thr Gly Met Gly Gly
  1               5                  10                  15

GCA GGG AAA ACT GTA GCC ATT CAG TCC TTC GAG GAT CTA GGT TAT TTC      96
Ala Gly Lys Thr Val Ala Ile Gln Ser Phe Glu Asp Leu Gly Tyr Phe
             20                  25                  30

ACC ATT GAT AAT ATG CCG CCA GCT CTC TTG CCT AAG TTT TTG CAG CTG     144
Thr Ile Asp Asn Met Pro Pro Ala Leu Leu Pro Lys Phe Leu Gln Leu
         35                  40                  45

GTT GAA ATT AAG GAA GAC AAT CCT AAG TTG GCC TTG GTA GTG GAT ATG     192
Val Glu Ile Lys Glu Asp Asn Pro Lys Leu Ala Leu Val Val Asp Met
     50                  55                  60

CGT AGT CGT TCT TTC TTT TCA GAG ATT CAA GCT GTT TTG GAT GAG TTG     240
Arg Ser Arg Ser Phe Phe Ser Glu Ile Gln Ala Val Leu Asp Glu Leu
 65                  70                  75                  80

GAA AAT CAA GAT GGT TTG GAT TTC AAA ATC CTC TTT TTG GAT GCG GCT     288
Glu Asn Gln Asp Gly Leu Asp Phe Lys Ile Leu Phe Leu Asp Ala Ala
                 85                  90                  95

GAT AAG GAA TTG GTC GCT CGT TAC AAG GAA ACC AGA CGG AGT CAC CCA     336
Asp Lys Glu Leu Val Ala Arg Tyr Lys Glu Thr Arg Arg Ser His Pro
            100                 105                 110

CTA GCA GCA GAC GGT CGT ATT TTA GAT GGA ATC AAG TTG GAA CGT GAA     384
Leu Ala Ala Asp Gly Arg Ile Leu Asp Gly Ile Lys Leu Glu Arg Glu
        115                 120                 125

CTC TTG GCA CCT TTG AAA AAT ATG AGC CAA AAT GTG GTG GAT ACG ACT     432
Leu Leu Ala Pro Leu Lys Asn Met Ser Gln Asn Val Val Asp Thr Thr
    130                 135                 140

GAA CTC ACT CCA CGT GAG CTG CGC AAA ACC CTT GCA GAG CAG TTT TCA     480
Glu Leu Thr Pro Arg Glu Leu Arg Lys Thr Leu Ala Glu Gln Phe Ser
145                 150                 155                 160

GAC CAA GAA CAA GCT CAG TCT TTC CGT ATC GAA GTC ATG TCT TTC GGA     528
Asp Gln Glu Gln Ala Gln Ser Phe Arg Ile Glu Val Met Ser Phe Gly
                165                 170                 175

TTT AAG TAT GGA ATC CCG ATT GAT GCG GAC TTG GTC TTT GAT GTC CGT     576
Phe Lys Tyr Gly Ile Pro Ile Asp Ala Asp Leu Val Phe Asp Val Arg
            180                 185                 190

TTC TTG CCA AAT CCC TAT TAT TTA CCA GAA CTG AGA AAC CAA ACG GGT     624
Phe Leu Pro Asn Pro Tyr Tyr Leu Pro Glu Leu Arg Asn Gln Thr Gly
        195                 200                 205
```

```
GTG GAT GAA CCT GTT TAT GAT TAT GTC ATG AAC CAT CCT GAG TCA GAA       672
Val Asp Glu Pro Val Tyr Asp Tyr Val Met Asn His Pro Glu Ser Glu
    210                 215                 220

GAC TTT TAT CAA CAT TTA TTG GCC TTG ATT GAG CCG ATT CTG CCA AGT       720
Asp Phe Tyr Gln His Leu Leu Ala Leu Ile Glu Pro Ile Leu Pro Ser
225                 230                 235                 240

TAC CAA AAG GAA GGT AAG TCC GTT TTG ACC ATT GCC ATG GGA TGT ACG       768
Tyr Gln Lys Glu Gly Lys Ser Val Leu Thr Ile Ala Met Gly Cys Thr
                245                 250                 255

GGT GGA CAA CAC CGT AGT GTG GCA TTT GCT AAA CGC TTG GTG CAG GAC       816
Gly Gly Gln His Arg Ser Val Ala Phe Ala Lys Arg Leu Val Gln Asp
            260                 265                 270

TTA TCC AAG AAT TGG TCT GTT AAT GAA GGG CAT CGC GAC AAA GAC CGC       864
Leu Ser Lys Asn Trp Ser Val Asn Glu Gly His Arg Asp Lys Asp Arg
        275                 280                 285

AGA AAG GAA ACG GTA AAC CGT TCA TGA                                   891
Arg Lys Glu Thr Val Asn Arg Ser  *
    290                 295
```

(2) INFORMATION FOR SEQ ID NO:2:

(i) SEQUENCE CHARACTERISTICS:
        (A) LENGTH: 296 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Lys Lys Gln Leu His Leu Val Ile Val Thr Gly Met Gly Gly
1               5                   10                  15

Ala Gly Lys Thr Val Ala Ile Gln Ser Phe Glu Asp Leu Gly Tyr Phe
                20                  25                  30

Thr Ile Asp Asn Met Pro Pro Ala Leu Leu Pro Lys Phe Leu Gln Leu
            35                  40                  45

Val Glu Ile Lys Glu Asp Asn Pro Lys Leu Ala Leu Val Val Asp Met
        50                  55                  60

Arg Ser Arg Ser Phe Phe Ser Glu Ile Gln Ala Val Leu Asp Glu Leu
65                  70                  75                  80

Glu Asn Gln Asp Gly Leu Asp Phe Lys Ile Leu Phe Leu Asp Ala Ala
                85                  90                  95

Asp Lys Glu Leu Val Ala Arg Tyr Lys Glu Thr Arg Arg Ser His Pro
            100                 105                 110

Leu Ala Ala Asp Gly Arg Ile Leu Asp Gly Ile Lys Leu Glu Arg Glu
        115                 120                 125

Leu Leu Ala Pro Leu Lys Asn Met Ser Gln Asn Val Val Asp Thr Thr
    130                 135                 140

Glu Leu Thr Pro Arg Glu Leu Arg Lys Thr Leu Ala Glu Gln Phe Ser
145                 150                 155                 160

Asp Gln Glu Gln Ala Gln Ser Pro Arg Ile Glu Val Met Ser Phe Gly
                165                 170                 175

Phe Lys Tyr Gly Ile Pro Ile Asp Ala Asp Leu Val Phe Asp Val Arg
            180                 185                 190

Phe Leu Pro Asn Pro Tyr Tyr Leu Pro Glu Leu Arg Asn Gln Thr Gly
        195                 200                 205

Val Asp Glu Pro Val Tyr Asp Tyr Val Met Asn His Pro Glu Ser Glu
    210                 215                 220
```

```
Asp Phe Tyr Gln His Leu Leu Ala Leu Ile Glu Pro Ile Leu Pro Ser
225                 230                 235                 240

Tyr Gln Lys Glu Gly Lys Ser Val Leu Thr Ile Ala Met Gly Cys Thr
            245                 250                 255

Gly Gly Gln His Arg Ser Val Ala Phe Ala Lys Arg Leu Val Gln Asp
                260                 265                 270

Leu Ser Lys Asn Trp Ser Val Asn Glu Gly His Arg Asp Lys Asp Arg
            275                 280                 285

Arg Lys Glu Thr Val Asn Arg Ser
    290                 295
```

(2) INFORMATION FOR SEQ ID NO:3:

(i) SEQUENCE CHARACTERISTICS:
        (A) LENGTH: 891 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:3:

```
AUGACAAAGA AACAACUUCA CUUGGUGAUU GUGACAGGGA UGGGUGGCGC AGGGAAAACU    60

GUAGCCAUUC AGUCCUUCGA GGAUCUAGGU UAUUUCACCA UUGAUAAUAU GCCGCCAGCU   120

CUCUUGCCUA AGUUUUUGCA GCUGGUUGAA AUUAAGGAAG ACAAUCCUAA GUUGGCCUUG   180

GUAGUGGAUA UGCUAGUCG UUCUUUCUUU UCAGAGAUUC AAGCUGUUUU GGAUGAGUUG    240

GAAAAUCAAG AUGGUUUGGA UUUCAAAAUC CUCUUUUUGG AUGCGGCUGA UAAGGAAUUG   300

GUCGCUCGUU ACAAGGAAAC CAGACGGAGU CACCCACUAG CAGCAGACGG UCGUAUUUUA   360

GAUGGAAUCA AGUUGGAACG UGAACUCUUG GCACCUUUGA AAAAUAUGAG CCAAAAUGUG   420

GUGGAUACGA CUGAACUCAC UCCACGUGAG CUGCGCAAAA CCCUUGCAGA GCAGUUUUCA   480

GACCAAGAAC AAGCUCAGUC UUUCCGUAUC GAAGUCAUGU CUUUCGGAUU UAAGUAUGGA   540

AUCCCGAUUG AUGCGGACUU GGUCUUUGAU GUCCGUUUCU UGCCAAAUCC CUAUUAUUUA   600

CCAGAACUGA GAAACCAAAC GGGUGUGGAU GAACCUGUUU AUGAUUAUGU CAUGAACCAU   660

CCUGAGUCAG AAGACUUUUA UCAACAUUUA UUGGCCUUGA UUGAGCCGAU UCUGCCAAGU   720

UACCAAAAGG AAGGUAAGUC CGUUUUGACC AUUGCCAUGG GAUGUACGGG UGGACAACAC   780

CGUAGUGUGG CAUUUGCUAA ACGCUUGGUG CAGGACUUAU CCAAGAAUUG GUCUGUUAAU   840

GAAGGGCAUC GCGACAAAGA CCGCAGAAAG GAAACGGUAA ACCGUUCAUG A            891
```

(2) INFORMATION FOR SEQ ID NO:4:

(i) SEQUENCE CHARACTERISTICS:
        (A) LENGTH: 913 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

```
AAACACTGCT TCTTGAGCGA ATGACGCTTT GTCCTTTTAA TGAGGTTACC AACGGCTTCA        60

AAGAGGATTC CCAGCTCGTT CAGCTGTGGA GGTAGCTCGT CTTCCTCGTG ATGTAAAAGT       120

CGAAATTGAA GTCATCGCAG AGATTGGATA AGCTAGTTGA AGTTTGGTGT TGCCAAACTT       180

CTTTTGATAT AAGGAGAAAA AGATGACAAA GAAACAACTT CACTTGGTGA TTGTGACAGG       240

GATGGGTGGC GCAGGGAAAA CTGTAGCCAT TCAGTCCTTC GAGGATCTAG GTTATTTCAC       300

CATTGATAAT ATGCCGCCAG CTCTCTTGCC TAAGTTTTTG CAGCTGGTTG AAATTAAGGA       360

AGACAATCCT AAGTTGGCCT TGGTAGTGGA TATGCGTAGT CGTTCTTTCT TTTCAGAGAT       420

TCAAGCTGTT TTGGATGAGT TGGAAAATCA AGATGGTTTG GATTTCAAAA TCCTCTTTTT       480

GGATGCGGCT GATAAGGAAT TGGTCGCTCG TTACAAGGAA ACCAGACGGA GTCACCCACT       540

AGCAGCAGAC GGTCGTATTT TAGATGGAAT CAAGTTGGAA CGTGAACTCT TGGCACCTTT       600

GAAAAATATG AGCCAAAATG TGGTGGATAC GACTGAACTC ACTCCACGTG AGCTGCGCAA       660

AACCCTTGCA GAGCAGTTTT CAGACCAAGA ACAAGCTCAG TCTTTCCGTA TCGAAGTCAT       720

GTCTTTCGGA TTTAAGTATG GAATCCCGAT TGATGCGGAC TTGGTCTTTG ATGTCCGTTT       780

CTTGCCAAAT CCCTATTATT TACCAGAACT GAGAAACCAA ACGGGTGTGG ATGAACCTGT       840

TTATGATTAT GTCATGAACC ATCCTGAGTC AGAAGACTTT TATCAACATT TATTGGCCTT       900

GATTGAGCCG ATT                                                         913
```